US012773259B2

(12) United States Patent
Choi

(10) Patent No.: US 12,773,259 B2
(45) Date of Patent: Oct. 27, 2026

(54) MONOPOLAR HANDPIECE FOR ELECTROSURGERY

(71) Applicants: In-Sang Choi, Uiwang-si (KR); Eun A Choi, Anyang-si (KR); Bo Hwan Choi, Seongnam-si (KR)

(72) Inventor: In-Sang Choi, Uiwang-si (KR)

(73) Assignees: In-Sang Choi, Uiwang-si (KR); Eun A Choi, Anyang-si (KR); Bo Hwan Choi, Seongnam-si (KR)

( * ) Notice: Subject to any disclaimer, the term of this patent is extended or adjusted under 35 U.S.C. 154(b) by 174 days.

(21) Appl. No.: 18/730,287

(22) PCT Filed: Jan. 25, 2022

(86) PCT No.: PCT/KR2022/001273
§ 371 (c)(1),
(2) Date: Jul. 18, 2024

(87) PCT Pub. No.: WO2023/145979
PCT Pub. Date: Aug. 3, 2023

(65) Prior Publication Data

US 2025/0127557 A1 Apr. 24, 2025

(51) Int. Cl.

*A61B 18/12* (2006.01)
*A61B 18/14* (2006.01)
*A61B 18/00* (2006.01)

(52) U.S. Cl.

CPC .. *A61B 18/148* (2013.01); *A61B 2018/00595* (2013.01); *A61B 2018/00601* (2013.01); *A61B 2018/0091* (2013.01); *A61B 2018/1253* (2013.01); *A61B 2218/008* (2013.01)

(58) Field of Classification Search

CPC ......... A61B 18/00; A61B 18/08; A61B 18/12; A61B 18/14; A61B 18/1402; A61B 18/148; A61B 2018/00178; A61B 2018/00202; A61B 2018/00595; A61B 2018/00601; A61B 2018/0091; A61B 2018/1253; A61B 2018/1475

See application file for complete search history.

(56) References Cited

U.S. PATENT DOCUMENTS 5,242,442 A * 9/1993 Hirschfeld ......... A61B 18/1402 606/49
5,849,022 A * 12/1998 Sakashita ............... A61B 17/29 606/174
2011/0098733 A1* 4/2011 Huynh ................... H01R 39/00 606/1
2014/0081086 A1* 3/2014 Shvetsov ............... A61B 90/98 600/249

(Continued)

FOREIGN PATENT DOCUMENTS

KR 10-2015-0113556 A 10/2015
KR 10-2020-0055535 A 5/2020

(Continued)

*Primary Examiner* — Daniel W Fowler
(74) *Attorney, Agent, or Firm* — NSIP Law

(57) ABSTRACT

The present invention relates to a handpiece for electrosurgery, the handpiece allowing direction and length of a working rod to be freely controlled during surgery, and effectively suctioning and removing smog that has negative health effects and obstructs the field of view of operating surgeons.

8 Claims, 7 Drawing Sheets

(56) References Cited

U.S. PATENT DOCUMENTS

| | | | | |
|---|---|---|---|---|
| 2016/0051314 | A1* | 2/2016 | Batchelor | A61B 18/1442 606/45 |
| 2019/0110832 | A1 | 4/2019 | Simonsen | |
| 2019/0216539 | A1* | 7/2019 | Choi | A61B 18/1402 |
| 2020/0246057 | A1* | 8/2020 | Park | A61B 18/14 |
| 2021/0393318 | A1* | 12/2021 | Williams | A61B 18/1445 |

FOREIGN PATENT DOCUMENTS

| | | | |
|---|---|---|---|
| KR | 10-2020-0137663 | A | 12/2020 |
| KR | 10-2021-0010391 | A | 1/2021 |

* cited by examiner

MONOPOLAR HANDPIECE FOR ELECTROSURGERY

TECHNICAL FIELD

The present disclosure relates to a handpiece for electrosurgery capable of freely adjusting the length and direction of a working rod during surgery and effectively suctioning and removing smoke that obstructs the operating surgeon's vision and has a bad influence on health.

BACKGROUND ART

Although iron scalpels are widely used in surgical operations, iron scalpels do not have a coagulation effect.

In other words, iron surgical scalpels cause bleeding when cutting tissue until the incision is completed or blood coagulates naturally in the incision site.

Electrosurgery is a surgical method that uses high frequency (radio frequency) electric energy to cut, excise, or cauterize a patient's tissue.

The high frequency electric energy supplied through the electrode causes vibrations in the cell, which in turn increases the temperature in the cell and heats the tissue.

When the temperature in the cell reaches about 60 degrees C., cell death occurs, and when heated to 60 to 90 degrees C., drying (dehydration) of the tissue and protein coagulation occur, and when the temperature in the cell reaches 100 degrees C., expansion of cell volume and vaporization occur, the so that tissue is cut or cauterized during this process.

This type of electrosurgery, as shown in FIG. 1, uses a a control unit 20 that generates high-frequency electric current for tissue incision and coagulation, and a handpiece 30 that incises, excises, and cauterizes tissue using the high-frequency electric energy, and the incision using the electrosurgical device generates heat during the tissue incision process by high-frequency electric current, resulting in a significant coagulation effect.

However, electrosurgical incision inevitably generates an arc accompanied by high heat when the air insulation layer is destroyed due to incomplete contact between the conductive electrode and the tissue, and the tissue burns and carbonizes by this arc to produce smog, which is known to have adverse effects on the health of the operating surgeon and the patient, as well as obscuring the operating surgeon's vision.

In addition, the length and rotation angle of the working rod to which the electrode is connected must be adjusted from time to time depending on conditions such as the depth and angle of the surgical site. To this end, the length and rotation of the working rod must be freely adjustable, and the adjusted working rod must be firmly fixed.

DISCLOSURE OF INVENTION

Technical Problem

The present disclosure is to provide a monopolar handpiece for electrosurgery capable of allowing an operating surgeon to freely adjust the length and rotation angle of a working rod during surgery, firmly fastening and fixing the adjusted working rod, and suctioning and processing smog generated during surgery without a separate suction device.

Solution to Problem

In view of the foregoing, a monopolar handpiece for electrosurgery according to the present disclosure includes a case (110); a cylindrical working rod (140) having a conductive electrode (180) fastened to a front end and a pogo pin (144) formed at a rear end to be electrically connected to the conductive electrode (180), and inserted into the case (110); a slider (150) formed to be rotatably fastened to the rear end of the working rod (140); a conductive member (154) fastened to the slider (150) so as to remain in electrical contact with the pogo pin (144) while the working rod (140) is rotating; and a coil cable (160) formed by a twisted cable in a thin film shape and configured to supply high-frequency electric energy to the conductive member (154), wherein the working rod (140) is configured to protrude from or be inserted into the case (110), adjusting the protrusion length, or rotate to adjust the surgical angle.

In this case, it is preferable that a pair of elastic pieces (141) having a fixing protrusion (142) protruding therefrom is formed in a semi-cylindrical shape at the rear end of the working rod (140) to be spaced a predetermined distance apart from each other, and that the elastic pieces (141) are configured to be inserted into and fastened in an insertion hole (151) of the slider (150).

In addition, it is preferable that the outer diameter of the slider (150) and the outer diameter of the working rod (140) are configured to be the same.

In addition, it is preferable that a guide protrusion (152) protrudes from one side of the slider (150), and that the guide protrusion (152) is inserted into a guide portion (116) formed in a long groove shape in the axial direction inside the case (110).

In this case, it is preferable that the conductive member (154) is configured to have a conductive body fastened to the slider (150), a pin contact portion (155) formed in a ring shape on one side of the body and in contact with a pogo pin (144), and a connector (156) formed on the other side of the body and connected to the coil cable (160).

In addition, it is preferable that a guide protrusion groove (157) is formed to perforate the body of the conductive member (154), and that the guide protrusion (152) of the slider (150) is inserted into the guide protrusion groove (157) so that the conductive member (154) is fastened to the slider (150).

In addition, it is preferable that the case (110) further include a working-rod fixing device configured to fix the working rod (140).

Advantageous Effects of Invention

The handpiece of the present disclosure configured above is able to freely adjust the length of the working rod to which the electrode is fastened during surgery, infinitely rotate the working rod regardless of the rotational direction to adjust the rotation angle and firmly fix the same, and suction and process smog generated during surgery without a separate suction device.

<Description of Reference Numerals>

Figure 1:
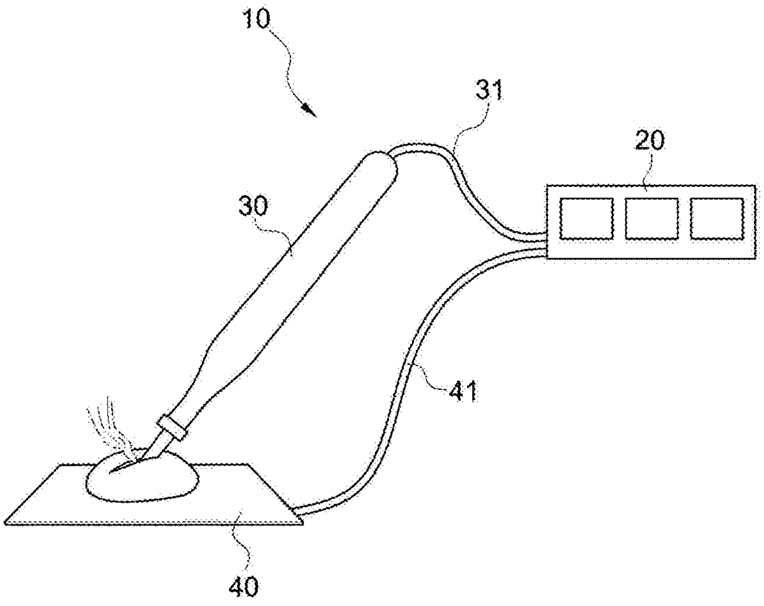
FIG. 1 is a diagram illustrating a monopolar electrosurgical device.

| | |
|---|---|
| 100: Handpiece | 101: Suction pipe |
| 102: Protection tube | 103: Plug |
| 110: Case | 111: Close-contact piece |
| 112: Pressing piece | 113: Protrusion |
| 114: Button | 115: Fastening groove |
| 116: Guide portion | 120: Locking member |
| 121: Pressing protrusion | 130: Inner case |
| 131: PCB | 132: Contact point |
| 140: Working rod | 141: Elastic piece |
| 142: Fixing protrusion | 143: Suction pipe insertion hole |
| 144: Pogo pin | 145: Conductive cable |
| 150: Slider | 151: Insertion hole |
| 152: guide protrusion | 153: Fixing protrusion |
| 154: Conductive member | 155: Pin contact portion |
| 156: Connector | 157: Guide protrusion groove |
| 158: Fixing protrusion groove | 160: Coil cable |
| 170: Rotator | 171: Fastening protrusion |
| 180: Conductive electrode | 181: Head |
| 182: Suction hole | 183: Electrode insertion hole |
| 184: Cover | |

BEST MODE FOR CARRYING OUT THE INVENTION

Hereinafter, the present disclosure will be described in detail with reference to preferred embodiments of the present disclosure and the attached drawings, on the premise that the same reference numerals in the drawings indicate the same elements.

The expression that one element "includes" another element in the detailed description of the invention or claims should be understood that one element may further include other elements, instead of being limitedly interpreted that one element includes only the relevant element, unless otherwise stated.

The terms "upper", "lower", "bottom", "front", "rear", "below", or the like used in this specification indicate the orientation of the elements as shown in the drawings for the purpose of facilitating explanation.

Figure 2:
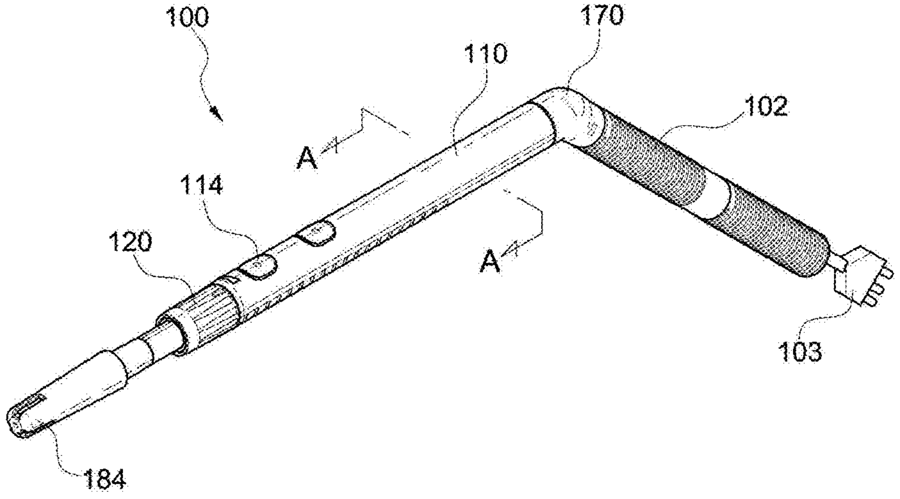
FIG. 2 is a perspective view illustrating a handpiece according to the present disclosure.
Figure 3:
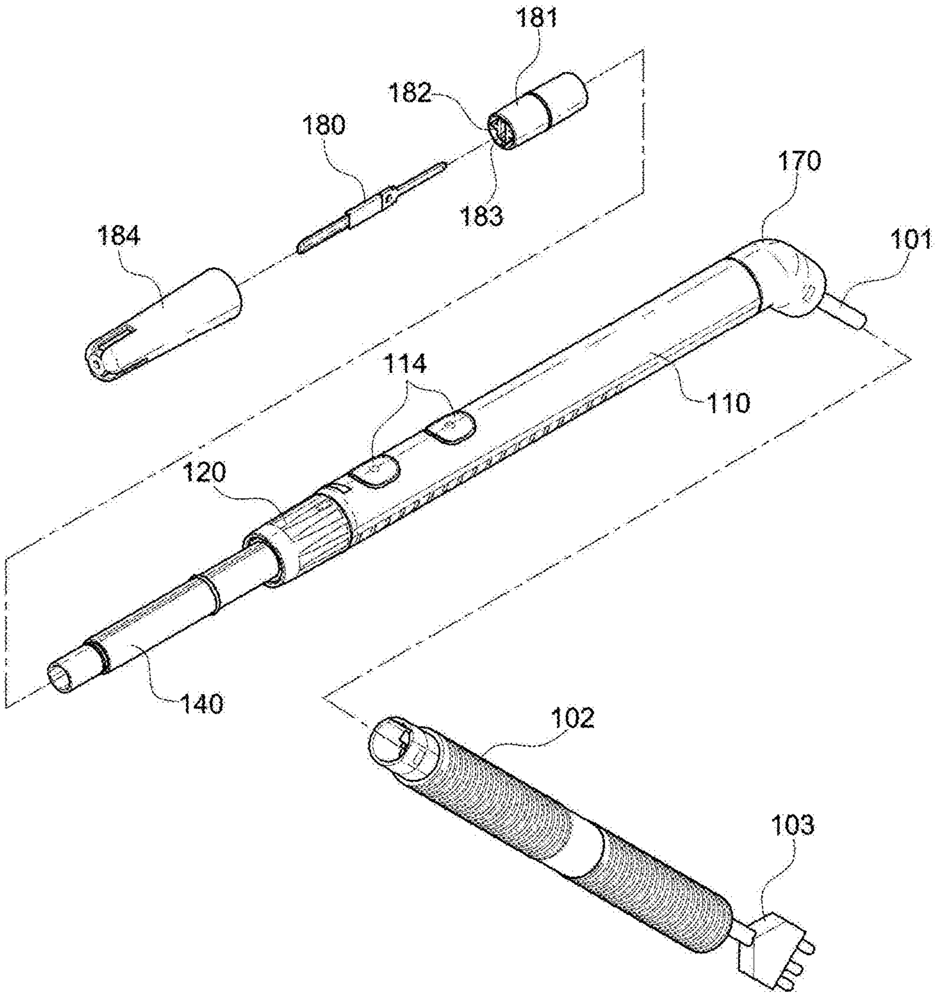
FIGS. 3 and 4 are exploded perspective views illustrating a handpiece according to the present disclosure.
Figure 4:
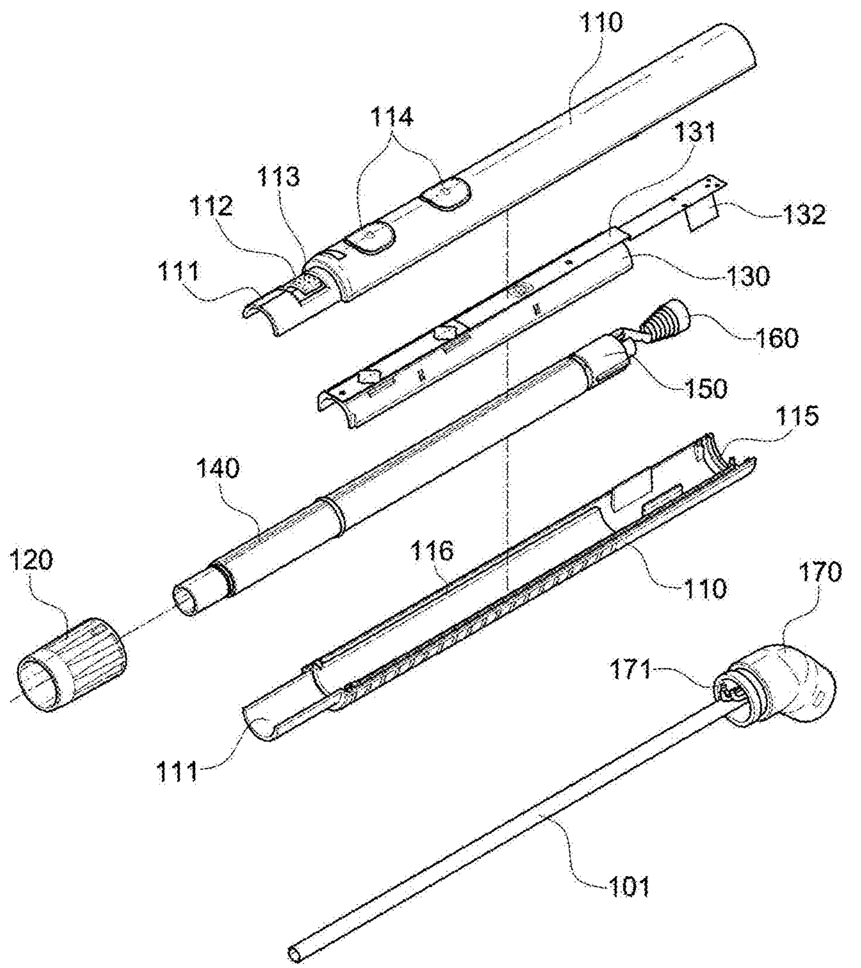
Figure 5:
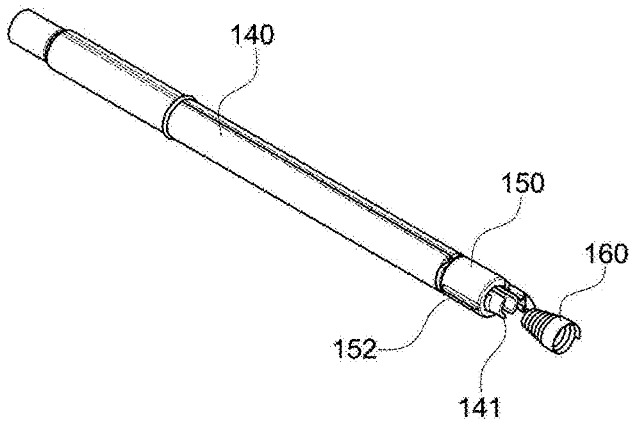
FIG. 5 is a perspective view illustrating a working rod constituting a handpiece of the present disclosure.

A handpiece 100 according to the present disclosure, as shown in FIGS. 2 to 4, is configured to include a case 110, a working rod 140 that retracts into or protrudes from the case 110 while being inserted into the case 110 to rotate relative to the case 110, a conductive electrode 180 fastened to the working rod 140, and a rotator 170 fastened to the rear end of the case 110 to rotate.

The working rod 140 with the conductive electrode 180 fastened to the front end thereof is inserted into the case 110 of the handpiece 100 so as to slide forward and backward or rotate, and the operating surgeon adjusts the degree of protrusion and the rotation angle of the conductive electrode 180 depending on the surgical conditions such as the depth and angle of the surgical site, and then rotates the locking member 120 so that the working rod 140 is fixed.

The working rod 140 has a cylindrical body having a rear end to which a slider 150 with a coil cable 160 fastened thereto is coupled as shown in FIG. 4, and a front end equipped with a head 181 having an electrode insertion hole 183 into which the conductive electrode 180 is inserted as shown in FIG. 3.

Figure 7:
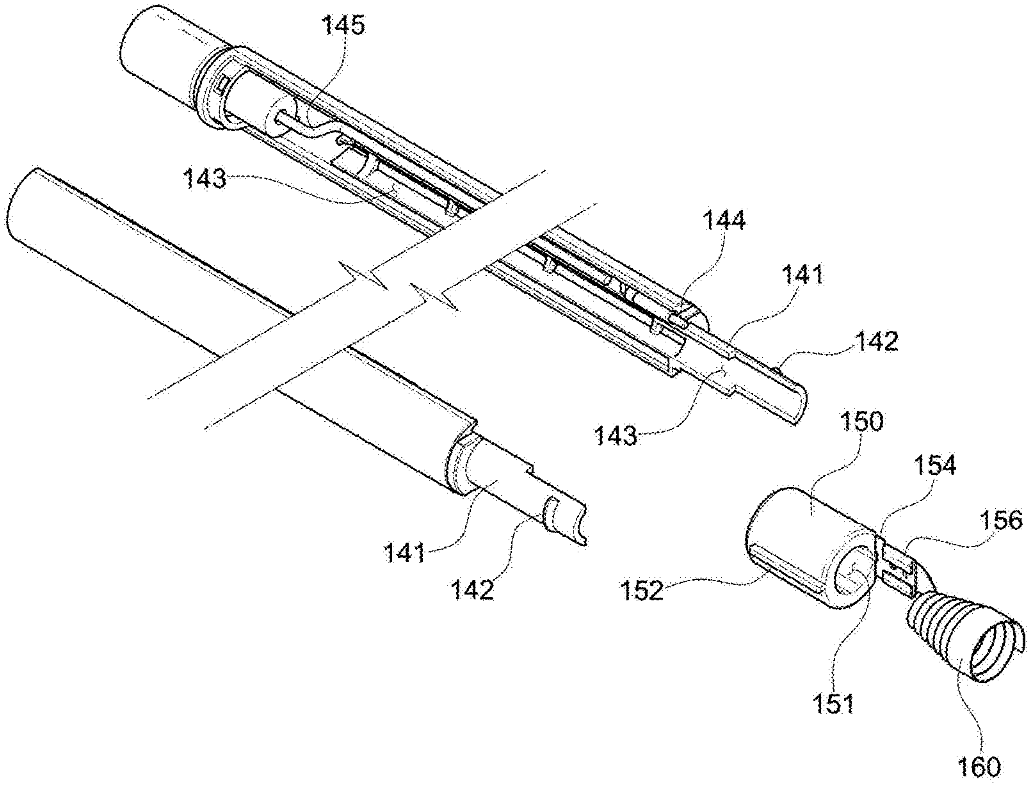
FIG. 7 is an exploded perspective view illustrating a working rod.

The coil cable 160 is configured as a twisted cable in a thin film shape to be elastically deformed, and is electrically connected to the contact point 132 of a PCB 131 shown in FIG. 4 and supplies high-frequency energy to the conductive electrode 180 through a conductive cable 145 inside the working rod 140 shown in FIG. 7.

In this case, the PCB 131 is connected to a control unit 20 through a conductive cable 31 as shown in FIG. 1.

The working rod 140 of the present disclosure protrudes from the case 110, is inserted into the case 110, or rotates depending on the surgical site and conditions, and at this time, the coil cable 160 elastically continue to supply high-frequency energy to the conductive electrode 180 while being deformed.

Figure 6:
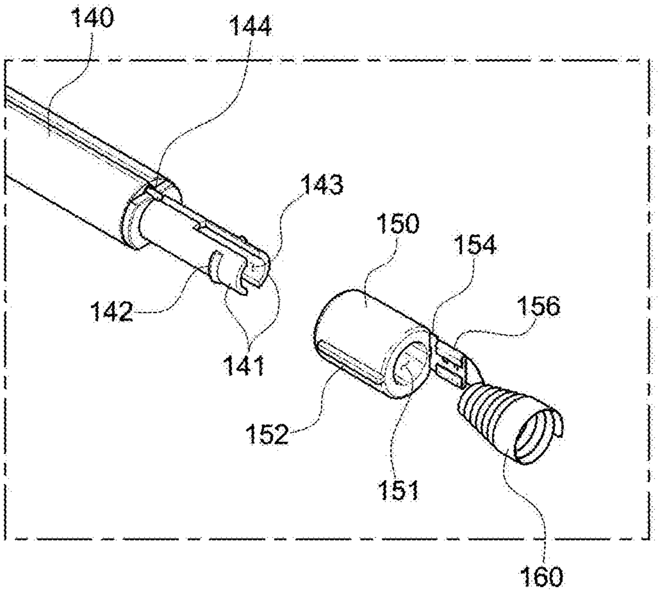
FIG. 6 is an enlarged perspective view illustrating the primary part of a working rod.

As shown in FIG. 6, the slider 150 is fastened to the rear end of the working rod 140 and has a cylindrical body that has a connector 156 formed to be electrically connected to the coil cable 160, and guide protrusions 152 protrude from both sides of the body of the slider 150.

Figure 8:
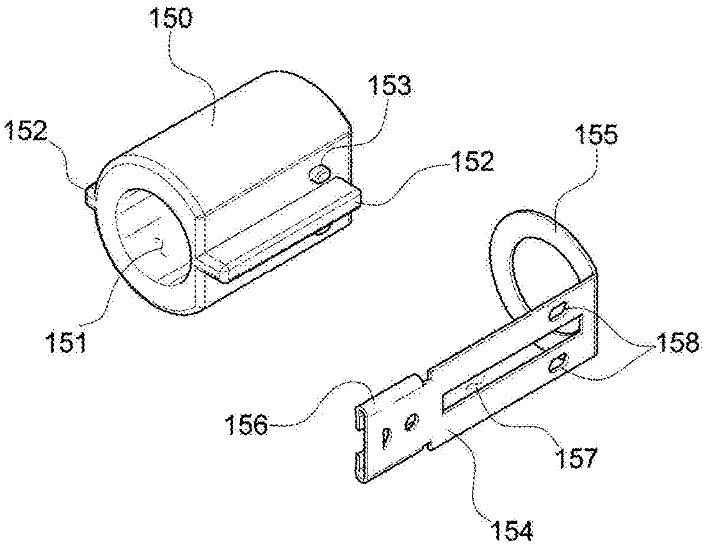
FIG. 8 is an exploded perspective view illustrating a slider of a working rod.

In addition, as shown in FIG. 8, a conductive member 154 is fastened to the slider 150. A connector 156 connected to the coil cable 160 is formed on one side of the body of the conductive member 154, and a pin contact portion 155 is formed in a ring shape on the other side of the body. In addition, a guide protrusion groove 157 and a fixing protrusion groove 158 are formed to perforate the body.

One guide protrusion 152 of the slider 150 is inserted into the guide protrusion groove 157 of the conductive member 15, and the fixing protrusions 153 formed on both sides of the guide protrusion 152 of the slider 150 are inserted into the fixing protrusion groove 158 of the conductive member 154, so that the slider 150 and the conductive member 154 are fastened.

As shown in FIGS. 6 and 7, a pair of elastic pieces 141 are formed at the rear end of the working rod 140 to be spaced a predetermined distance apart from each, forming a cylindrical shape, such that the outer diameter formed by the elastic pieces 141 is configured to be smaller than the outer diameter of the working rod 140, and the outer diameter formed by the elastic pieces 141 is configured to be equal to or greater by a predetermined value than the diameter of the insertion hole 151 of the slider 150.

In addition, as shown in FIG. 6, a pogo pin 144 elastically supported by a spring protrudes from the rear end of the working rod 140 (the tip of the elastic piece 141). The pogo pin 144 is electrically connected to the conductive electrode 180 through the conductive cable 145 inside the working rod 140.

As shown in FIG. 6, if the elastic pieces 141 are inserted into the insertion hole 151 of the slider 150, the pin contact portion 155 formed at the tip of the slider 150 comes into contact with the pogo pin 144 of the working rod 140, so that the coil cable 160 is electrically connected to the conductive electrode 180.

In addition, the working rod 140 may rotate freely relative to the slider 150, and the pogo pin 144 remains in contact with the contact point 155 of the ring-shaped slider 150 while the working rod 140 is rotating.

Since the pair of elastic pieces 141 are spaced a predetermined distance apart from each other and have the fixing protrusion 142 protruding from the end, when the elastic pieces 141 are inserted into the insertion hole 151 of the slider 150, the elastic pieces 141 elastically deform and shrink, and elastically restore at the moment when the fixing protrusion 142 passes through the insertion hole 151 of the slider 150, so that the slider 150 is caught by the fixing protrusion 142 to be prevented from being separated from the working rod 140.

The slider 150 and the working rod 140 coupled to each other as described above are inserted into the case 110, and as shown in FIG. 4, a guide portion 116 is formed in the form of a step at the case fastening portion of one of separated upper and lower cases 110. In the embodiment of the present disclosure, the guide portion 116 is formed on the lower case 110.

Figure 9:
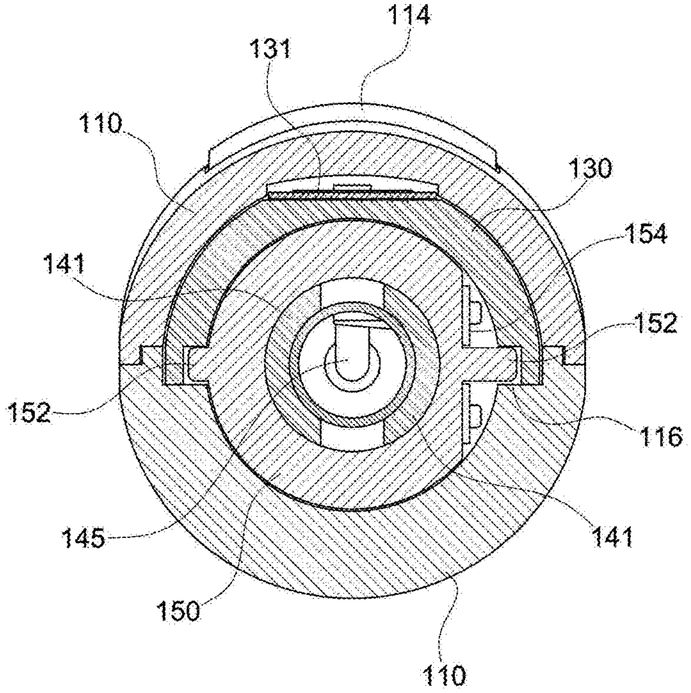
FIG. 9 is a cross-sectional view taken along line A-A in FIG. 2.

When the working rod 140 to which the slider 150 is fastened is inserted into the separated upper and lower cases 110 and then the upper and lower cases 110 are coupled, as shown in FIG. 9, the guide protrusion 152 of the slider 150 is positioned between the lower case 110 and the inner case 130, so that the slider 150 is able to slide along the guide portion 116.

As shown in FIG. 9, in the embodiment of the invention, although the guide protrusion 152 of the slider 150 is configured to be slidable by the lower case 110 and the inner case 130, it may also be configured to be slidable by the lower case 110 and the upper case 110.

When the working rod 140 combined with the case 110 configured above protrudes to the outside of the case 110 or is inserted into the case 110 depending on the depth of the surgical site, the guide protrusion 142 of the slider 150 slides along the guide portion 116 of the case 110 to guide the protrusion or insertion of the working rod 140, and the coil cable 160 fastened to the slider 150 elastically deforms or elastically restores and supplies high-frequency electric energy to the conductive electrode 180 even during the protrusion or insertion process of the working rod 140.

In addition, the working rod 140 is able to rotate to conform to the depth or angle of the surgical site, and when rotating the working rod 140, only the working rod 140 rotates in the state in which the slider 150 does not rotate and is fixed because the guide protrusion 153 is inserted into the guide portion 116.

Even if only the working rod 140 rotates, the pogo pin 144 of the working rod 140 remains in contact the pin contact portion 155, formed in a ring shape, of the slider 150, so that high-frequency electric energy is continuously supplied to the conductive electrode 180 even while the working rod 140 is rotating.

If the slider 150 rotates in conjunction with the working rod 140, the coil cable 160 may be twisted and damaged. However, since the working rod 140 of the present disclosure is configured such that only the working rod 140 rotates while the slider 150 does not rotate, it may rotate infinitely in the clockwise or counterclockwise direction while the coil cable 160 is not damaged.

In the embodiment of the present disclosure, although the guide protrusion 152 is described as protruding from both of sides the slider 150, respectively, but the guide protrusion 152 may be configured to protrude from only one side.

As described above, the handpiece 100 of the present disclosure may adjust the length and rotation angle of the working rod 140 of the handpiece 100 depending on the depth or angle of the surgical site, and the working rod must be fixed so as not to move after adjusting the length and angle. To this end, the present disclosure configures a working-rod fixing device.

As shown in FIG. 4, the working-rod fixing device of the present disclosure has a close-contact piece 111 and a pressing piece 112 formed at the tips of the upper and lower cases 110. The pressing piece 112 is formed by cutting the close-contact piece 111 in a ‘C’ shape so as to elastically deform relative to the close-contact piece 111.

Figure 10:
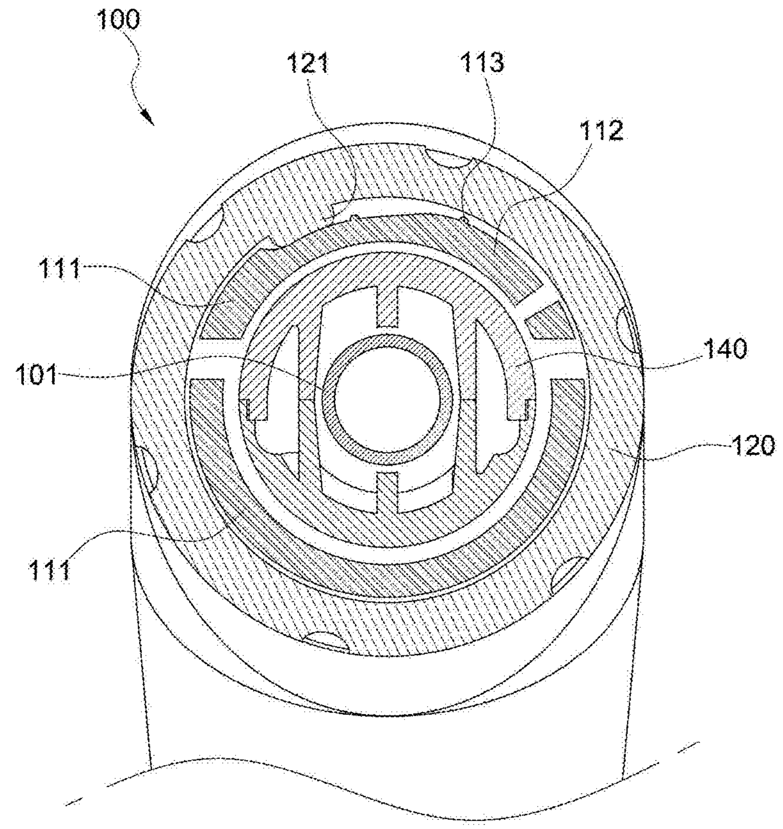
FIG. 10 is a cross-sectional view illustrating the unlocked state of a locking hole.

As shown in FIG. 10, the pressing piece 112 is formed such that the point connected to the close-contact piece 111 is thin and such that the thickness gradually increases toward the end, and protrusions 113 protrude at predetermined intervals.

The pressing piece 111 is inserted into the cylindrical locking member 120, and a pressing protrusion 121 protrudes from the inner surface of the locking member 120.

The length and angle of the working rod 140 are adjusted in the state in which the locking member 120 is released, and the state in which the locking member 120 is released indicates the state in which the pressing protrusion 121 of the locking member 120 is positioned at the point where the pressing piece 112 has a minimum thickness, as shown in FIG. 10.

In this state, since the pressing piece 112 does not come into contact with the working rod 140, the length and rotation angle of the working rod 140 may be freely adjusted.

Figure 11:
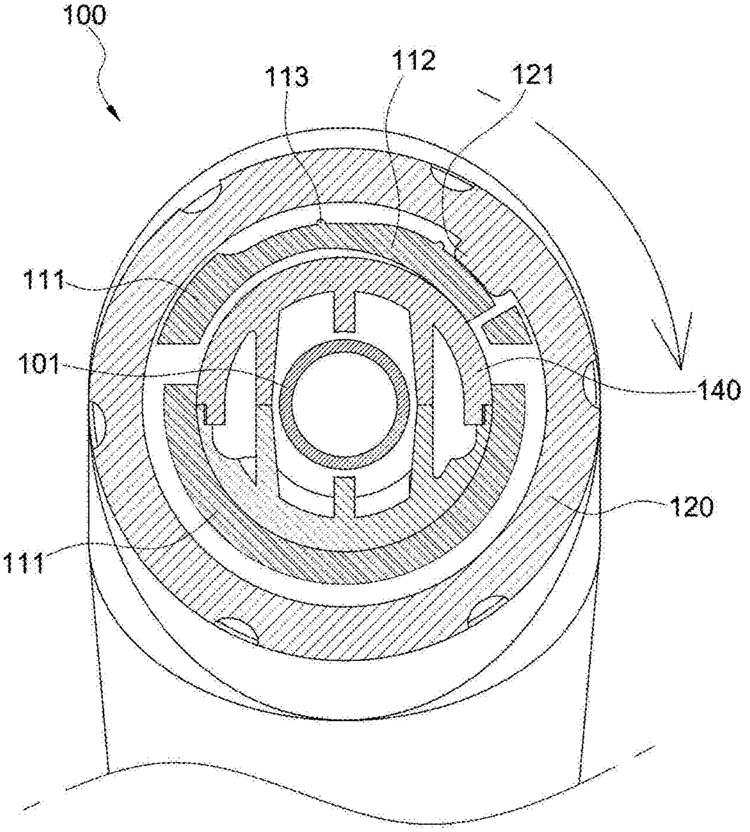
FIG. 11 is a cross-sectional view illustrating the locked state of a locking hole.

When the locking member 120 is rotated to fix the working rod 140 after adjusting the length and rotation angle of the working rod 140, as shown in FIG. 11, the pressing protrusion 121 of the locking member 120 moves to the thickest point of the pressing piece 112 and presses the pressing piece 112 inward, and the pressing piece 112 presses the working rod 140, thereby fixing the working rod 140.

At this time, the protrusion 113 of the pressing piece 112 provides a sense of distinction to the user when the pressing protrusion 121 passes over the protrusion 113 when the locking member 120 is rotated.

Tissue is cut or cauterized in the state in which the length and angle of the working rod 140 are adjusted and the working rod 140 is fixed by the locking member 120 as described above, and smog occurs at this time, which has a negative effect on the health of the operating surgeon or patient.

The present disclosure is configured to have a suction structure in which the handpiece suctions smog generated during surgery.

As shown in FIGS. 3 and 4, a suction pipe 101 is inserted into the protective tube 102 and inserted into the suction pipe insertion hole 143 inside the working rod 140 through the rotator 170.

In addition, as shown in FIG. 3, the head 181 into which the conductive electrode 180 is inserted is fastened to the tip of the working rod 140, and suction holes 182 are formed on both sides of the electrode insertion hole 183 of the head 181.

If smog is generated due to supply of high-frequency electric energy to the conductive electrode 180 during surgery, the smog is suctioned through the suction holes 182, and the suctioned smog is discharged through the suction pipe 101.

As shown in FIG. 4, a ring-shaped fastening groove 115 is formed at the end of the case 110, and a fastening protrusion 171 formed at the tip of the rotator 170 bent at a predetermined angle is inserted into the fastening groove 115 to be fastened, so that the rotator 170 rotates freely and does interfere with the operating surgeon’s operation even if the operating surgeon holds the handpiece 100 at an arbitrary angle and performs the operation.

The handpiece of the present disclosure configured above is able to freely adjust the length of the working rod to which the electrode is fastened during surgery, infinitely rotate the working rod regardless of the rotational direction to adjust the rotation angle and firmly fix the same, and suction and process smog generated during surgery without a separate suction device.

The technical idea of the present disclosure has been described through the above embodiment.

It is obvious for those skilled in the art to which the present disclosure pertains to modify or change the embodiment described above in various ways on the basis of the description of the present disclosure.

In addition, even if it is not explicitly illustrated or described, it is obvious for those skilled in the art to which the present disclosure pertains to make various modifications encompassing the technical idea of the present disclosure from the description of the present disclosure, which still falls within the scope of the present disclosure.

The above embodiment described with reference to the attached drawings has been described for the purpose of explaining the present disclosure, and the scope of the present disclosure is not limited to this embodiment.

The invention claimed is:

1. A monopolar handpiece for electrosurgery, comprising:

a case (110);

a cylindrical working rod (140) having a conductive electrode (180) fastened to a front end and a pogo pin (144) formed at a rear end to be electrically connected to the conductive electrode (180), and inserted into the case (110);

a slider (150) formed to be rotatably fastened to the rear end of the working rod (140);

a conductive member (154) fastened to the slider (150) configured to have a conductive body fastened to the slider (150), a pin contact portion (155) formed in a ring shape on one side of the body and in contact with the pogo pin (144), and a connector (156) formed on the other side of the body and connected to a coil cable (160), the conductive member (154) configured so as to remain in electrical contact with the pogo pin (144) while the working rod (140) is rotating; and the coil cable (160) formed by a twisted cable in a thin film shape and configured to supply high-frequency electric energy to the conductive member (154), wherein the working rod (140) is configured to protrude from or be inserted into the case (110), adjusting the protrusion length, or rotate to adjust the surgical angle.

2. The monopolar handpiece for electrosurgery of claim 1, wherein a pair of elastic pieces (141) having a fixing protrusion (142) protruding therefrom is formed in a semi-cylindrical shape at the rear end of the working rod (140) to be spaced a predetermined distance apart from each other, and the elastic pieces (141) are configured to be inserted into and fastened in an insertion hole (151) of the slider (150).

3. The monopolar handpiece for electrosurgery of claim 2, wherein the outer diameter of the slider (150) and the outer diameter of the working rod (140) are configured to be the same.

4. The monopolar handpiece for electrosurgery of claim 1, wherein a guide protrusion (152) protrudes from one side of the slider (150), and wherein the guide protrusion (152) is inserted into a guide portion (116) formed in a long groove shape in the axial direction inside the case (110).

5. The monopolar handpiece for electrosurgery of claim 1, wherein a guide protrusion groove (157) is formed to perforate the body of the conductive member (154), and wherein the guide protrusion (152) of the slider (150) is inserted into the guide protrusion groove (157) so that the conductive member (154) is fastened to the slider (150).

6. The monopolar handpiece for electrosurgery of claim 1, wherein the case (110) further comprises a working-rod fixing device configured to fix the working rod (140).

7. The monopolar handpiece for electrosurgery of claim 1, wherein a rotator (170) in the shape of a pipe bent at a predetermined angle is rotatably fastened to the rear end of the case (110), and a suction pipe (101) is inserted into a suction pipe insertion hole (143) inside the working rod (140) through the rotator (170).

8. The monopolar handpiece for electrosurgery of claim 7, wherein an electrode insertion hole (183) into which the conductive electrode (180) is inserted is formed at the tip of the working rod (140), and a head (181), having suction holes (182) formed in the shape of a hole on one or both sides of the electrode insertion hole (183) to suction smog, is fastened to the tip of the working rod (140).

* * * * *